US012773354B2

(12) United States Patent
Hagerty et al.

(10) Patent No.: US 12,773,354 B2
(45) Date of Patent: Oct. 27, 2026

(54) NURSING PAD SYSTEM

(71) Applicant: ASO LLC, Sarasota, FL (US)

(72) Inventors: Brooke A. Hagerty, Sarasota, FL (US); Mira Dosen, Sarasota, FL (US); Edmund A. Sinda, Bradenton, FL (US)

(73) Assignee: ASO LLC, Sarasota, FL (US)

( * ) Notice: Subject to any disclaimer, the term of this patent is extended or adjusted under 35 U.S.C. 154(b) by 995 days.

(21) Appl. No.: 17/699,815

(22) Filed: Mar. 21, 2022

(65) Prior Publication Data

US 2023/0293355 A1 Sep. 21, 2023

(51) Int. Cl.
*A61F 13/14* (2006.01)

(52) U.S. Cl.
CPC .................................. *A61F 13/141* (2013.01)

(58) Field of Classification Search
CPC ............ A61F 13/14; A61F 2013/15016; A61F 13/141; A41C 3/0035; A41C 3/144; A41C 3/04; A41C 3/12; A41C 3/10; A41C 5/00; A41C 3/00; A41C 5/005; A41C 3/08; A41C 3/0014; A41C 3/0007; A41C 3/0028; A41C 3/14; A41C 3/065; A41C 3/0057; A41C 3/02; A41C 3/005; A41C 3/148; A41C 3/0064; A41C 3/105; A41C 3/122; A41C 3/0085; A41C 1/06; A41C 3/0021; A41C 3/142; A41C 3/06; A41C 3/146; A41C 1/00; A41C 1/10; A41C 1/12; A41C 1/08; A41C 3/0071; A41C 3/0092; A41C 3/128; A41C 3/0078; A41C 3/124; A41C 3/0042; A41C 1/003; A41C 1/02; A41C 1/14; A61B 6/502; A61B 6/0414; A61B 5/4312; A61B 10/0041; A61H 2205/082; A61H 2201/165
See application file for complete search history.

(56) References Cited

U.S. PATENT DOCUMENTS

| | | | | |
|---|---|---|---|---|
| 4,992,074 | A * | 2/1991 | Diaz | A41C 3/065 450/55 |
| 5,919,180 | A * | 7/1999 | Raimondo | A61F 13/141 602/41 |
| 6,074,272 | A | 6/2000 | Hebert | |
| 6,241,715 | B1 | 6/2001 | Houser et al. | |
| 6,695,678 | B1 | 2/2004 | Foley et al. | |
| 6,875,200 | B1 | 4/2005 | Ajagbe | |
| 7,008,409 | B2 | 3/2006 | Spiezio et al. | |

(Continued)

FOREIGN PATENT DOCUMENTS

| | | | | |
|---|---|---|---|---|
| GB | 2577982 | * 5/2020 | | A41C 3/04 |
| WO | 96/41601 | * 12/1996 | | A61F 13/14 |

(Continued)

*Primary Examiner* — Michele Kidwell
(74) *Attorney, Agent, or Firm* — GrayRobinson, P.A.

(57) ABSTRACT

The present disclosure relates to a nursing pad system. The system consists of a base that is designed to be adhesively secured about the nipple of a breast feeding mother. A top cover, which is preferably disposable, is thereafter secured over top of the base component. The adhesive securing the base is preferably a low trauma adhesive. The adhesive securing the top cover is preferably a strong adhesive. The top cover includes an inner surface formed from an absorbent material and that includes a pocket. Milk is both absorbed by the inner surface and collected in the pocket. The top cover is designed to be separable from the base so that it can be replaced as needed.

42 Claims, 9 Drawing Sheets

(56) References Cited

U.S. PATENT DOCUMENTS

| | | | | |
|---|---|---|---|---|
| 7,396,339 | B2 | 7/2008 | Britto et al. | |
| 7,448,936 | B1 * | 11/2008 | Kemp-Dorsey | A41C 3/04 450/36 |
| 8,172,791 | B2 | 5/2012 | Callanan et al. | |
| 8,460,233 | B2 | 6/2013 | McCoy | |
| 8,523,804 | B2 | 9/2013 | Cudworth | |
| 8,911,417 | B2 | 12/2014 | Mundschau et al. | |
| 9,005,177 | B2 * | 4/2015 | Krasikoff | A61F 13/141 604/386 |
| 9,687,395 | B2 * | 6/2017 | Clarke | A41D 31/125 |
| 10,226,557 | B2 | 3/2019 | Dann | |
| 10,413,452 | B2 | 9/2019 | Estevanell | |
| 10,722,624 | B2 | 7/2020 | Makower et al. | |
| 11,206,875 | B2 * | 12/2021 | Morrow Contreras | A41C 3/065 |
| 2004/0154068 | A1 * | 8/2004 | Gorringe | A61F 13/141 2/104 |
| 2005/0186885 | A1 * | 8/2005 | Valentin | A41C 3/065 450/81 |
| 2006/0057938 | A1 * | 3/2006 | Huang | A61F 13/141 450/81 |
| 2009/0088717 | A1 | 4/2009 | Pawloski et al. | |
| 2009/0234315 | A1 | 9/2009 | Gomez | |
| 2011/0184344 | A1 * | 7/2011 | Baker-Jackson | A41D 1/215 604/73 |
| 2012/0259303 | A1 | 10/2012 | Carter | |
| 2014/0273737 | A1 | 9/2014 | Cortese et al. | |
| 2014/0302745 | A1 * | 10/2014 | Golubovic | A61F 13/145 450/1 |
| 2016/0007659 | A1 | 1/2016 | Blacker | |
| 2016/0095743 | A1 * | 4/2016 | Jackson | A61F 7/02 607/108 |
| 2017/0231840 | A1 | 8/2017 | Taylor | |
| 2018/0055696 | A1 * | 3/2018 | Smith | A61F 13/141 |
| 2019/0053962 | A1 | 2/2019 | Lavon | |
| 2019/0133832 | A1 * | 5/2019 | Langley | A61F 13/141 |
| 2021/0361473 | A1 * | 11/2021 | Crowe | H01M 10/425 |
| 2022/0117799 | A1 | 4/2022 | Westergren | |
| 2023/0414457 | A1 | 12/2023 | Qu et al. | |

FOREIGN PATENT DOCUMENTS

| | | | | |
|---|---|---|---|---|
| WO | 2001047452 A1 | | 7/2001 | |
| WO | 2009/043007 | * | 4/2009 | A61F 13/14 |
| WO | 2021/069888 | * | 4/2021 | A61F 13/14 |
| WO | 2021/099972 | * | 5/2021 | |

* cited by examiner

NURSING PAD SYSTEM

TECHNICAL FIELD

This disclosure relates to a nursing pad system. More particularly, the present disclosure relates to a nursing pad system that can be removably secured to a breast.

BACKGROUND OF THE INVENTION

Breastfeeding or nursing is a choice made by a mother to provide milk to her infant after birth. According to the CDC, out of the 2.2 million children born in the United States in 2020, approximately 83.9% were, at some point, breastfed. After one year, approximately 35% of those infants were still breastfed. Therefore, in the United States, approximately 1,800,000 women were breastfeeding in 2020 and 750,00 were still breastfeeding after one year.

After the birth of a child, levels of estrogen and progesterone fall in a mother, which enables another hormone, prolactin, to promote milk production. Initially, a mother produces colostrum, which is nutrient-rich, yellowish-colored milk which helps boost an infant's immune system. About three days after birth, a thinner and whiter milk is produced in larger amounts. This larger volume of milk is needed as infants require feeding about every two to three hours in their early life. In between feedings, a mother's breast may become engorged and will lactate due to pressure, stimulation, or the sound of a baby's cry (and not just her own). This results in the leaking of milk from a mother's breast.

The variation of leaking is different for different women and is based on the level of milk production. Different women produce different amounts of milk. For instance, mothers with twins may produce twice the amount of milk as a mother nursing one child. On average, women produce 25 to 35 ounces of milk each day, which again, can vary based on the amount of milk that is required. The level of lactation will also adjust based on how much milk is being used. As the infant develops, mothers will produce larger amounts of milk—up to 9 to 10 ounces—and will feed less often.

In between feedings, a mother may experience light to heavy leaking from her breasts. Therefore, nursing pads are recommended. Throughout the day, women should expect to use about three pairs of pads. Some disposable pads can hold approximately three ounces of milk prior to saturating clothing. Unfortunately, existing nursing pads cannot properly protect against such leaking.

One known type of nursing pad uses negative pressure to retain the milk. This design has been known to have numerous drawbacks, including irritations and injuries to the skin and blockages in the milk ducts. End-users have reported blisters on their nipple due to the negative pressure. Additionally, the skin can be torn, cracked, or chapped as a result of these pads. These pads can also trap bacteria and increase infection risks. Furthermore, inhibiting milk flow can cause the milk ducts to become clogged, which can lead to an infection known as mastitis. Mastitis is a bacterial infection which can be very painful for lactating mothers and can produce flu-like symptoms.

Reusable nursing pads are another type. While less dangerous, they are more inconvenient. Reusable pads do not have any adhesive ability, and therefore, shift beneath clothing. While shifting, these pads may rub against the nipple and stimulate further milk production. While the reusable pads are able to catch some of the milk that leaks, they are generally less absorptive, being made from cotton or bamboo. Additionally, they do not hold in any moisture and generally feel wet against the skin and clothing. Once a reusable pad is saturated, it can leak onto clothing where it can stain permanently, due to the presence of fats and oils within the milk. Leaking of breast milk in public locations, such as the workplace, can be embarrassing and uncomfortable for nursing mothers. Also, since the pads are able to shift due to lack of adhesion, the pad can be known to slip and become visible and non-discrete, depending on the users clothing.

Disposable nursing pads are often preferred by women in their first few months of breastfeeding due to the absorbency level being higher than reusable nursing pads. However, after the disposable pad becomes saturated, milk will begin to saturate clothing and pose the same risks as reusable pads. Disposable nursing pads may include adhesive tabs to hold the pads in place within a brassier. However, the adhesive tabs that secure the nursing pad to the brassier still enable rubbing and friction, which can lead to excess leakage. When the adhesive tabs become wet, they can also detach from the brassier and may fall out, becoming non-discrete.

An example of a specific type of leak guard is disclosed in WO 21018/204,681 to Caden, which discloses a moisture absorbing anti-leak garment. The garment is constructed to absorb fluids associated both sweat and lactation. The garment can be a bra with opposing pockets that receive circular absorption pads. These pads are fabricated from materials having prescribed moisture absorption properties. Likewise, WO 2016/054,645 to Jackson discloses a thermal device for treating breastfeeding conditions. The device is used in connection with a bra and includes a pouch made of a flexible material that is secured to a bra cup via a strap. A barrier member, which can be made of an absorbent material, is secured within the pouch via attachment means, disclosed as hook and pile fasteners. Jackson's barrier member can be soaked in a liquid prior to being secured within the pouch to provide moist heat therapy. Additionally, U.S. Pat. No. 10,744,025 to Osorio discloses an apparatus for passive milk collection. The apparatus is adapted to be worn with a brassiere. The apparatus is disclosed as being able to take the form of a cupped container having a concave inner surface and a convex outer surface. The apparatus may further include a lid with an opening for receiving a liquid.

The nursing pad system of the present disclosure overcomes the drawbacks, deficiencies, and unmet needs associated with these devices by addressing issues, such as, leaking, absorbency, hygiene, irritation, comfort, and milk flow regulation. The nursing pad system of the present disclosure is designed to overcome these and other shortcomings present in the background art.

SUMMARY OF THE INVENTION

This disclosure relates to a two-part nursing pad system.

The disclosed system has several important advantages. For example, the disclosed system includes a lower base that is adhered to a breast and a top cover that is, in turn, adhered to the lower base.

An important advantage of the present system is attained by forming the removable top cover from a milk absorbing material.

Another advantage is realized by providing a top cover that includes an interior pocket that sits beneath the nipple and collects any milk that is not otherwise absorbed.

A further advantage is attained by securing the base via a low trauma adhesive while at the same time securing the top cover via a strong bond adhesive.

Still yet another advantage is achieved by including a tab along an edge of the top cover, with the tab being used in separating the top cover from the lower base.

The disclosed system allows the mother's nipple to be readily exposed and separated from the pad for feeding by separating the top cover from the base.

The base is advantageously shaped into a U-shape such that it can conform to the mother's breast and surround the nipple.

Various embodiments of the invention may have none, some, or all of these advantages. Other technical advantages of the present invention will be readily apparent to one skilled in the art.

BRIEF DESCRIPTION OF THE DRAWINGS

For a more complete understanding of the present disclosure and its advantages, reference is now made to the following descriptions, taken in conjunction with the accompanying drawings, in which.

Similar reference numerals refer to similar parts throughout the several views of the drawings.

| Parts List |
|---|
| 20 Nursing Pad System |
| 22 Base Component |
| 24 Inner Surface of Base |

-continued

| Parts List |
|---|
| 26 Outer Surface of Base |
| 28 Interior Area of Base |
| 32 Adhesive (Low-Trauma) |
| 34 Top Cover |
| 36 Inner Surface Top Cover |
| 38 Outer Surface Top Cover |
| 42 Upper Extent Top Cover |
| 44 Lower Extent Top Cover |
| 46 Interior Area Top Cover |
| 48 Peripheral Areas of Top Cover |
| 52 Adhesive (Strong Bond) |
| 54 Pocket |
| 56 Inner Surface of Pocket |
| 58 Release Tab |
| 62 Alternative Embodiment of Pocket |
| 64 Flap between Base and Top Cover |

DETAILED DESCRIPTION OF THE DRAWINGS

The present disclosure relates to a nursing pad system. The system consists of a base and a top cover. The base is designed to be removably and adhesively secured about the nipple of a breast feeding mother. The top cover, which is preferably disposable, is adhesively secured to the base component. The adhesive of the base is preferably a low trauma adhesive; the adhesive of the top cover is preferably a strong bond adhesive. The top cover includes an absorbent inner surface with a pocket. This allows milk to be absorbed by the inner surface and collected in the pocket. The top cover is separable from the base so that it can be replaced as needed.

Figure 1:
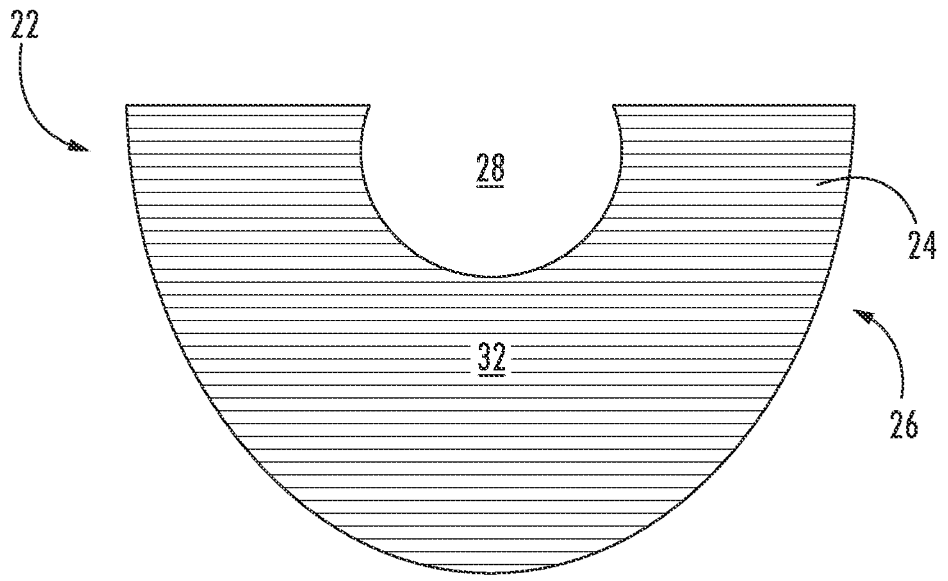
FIG. 1 is a plan view of the back side of the base component of the nursing pad system.
Figure 2:
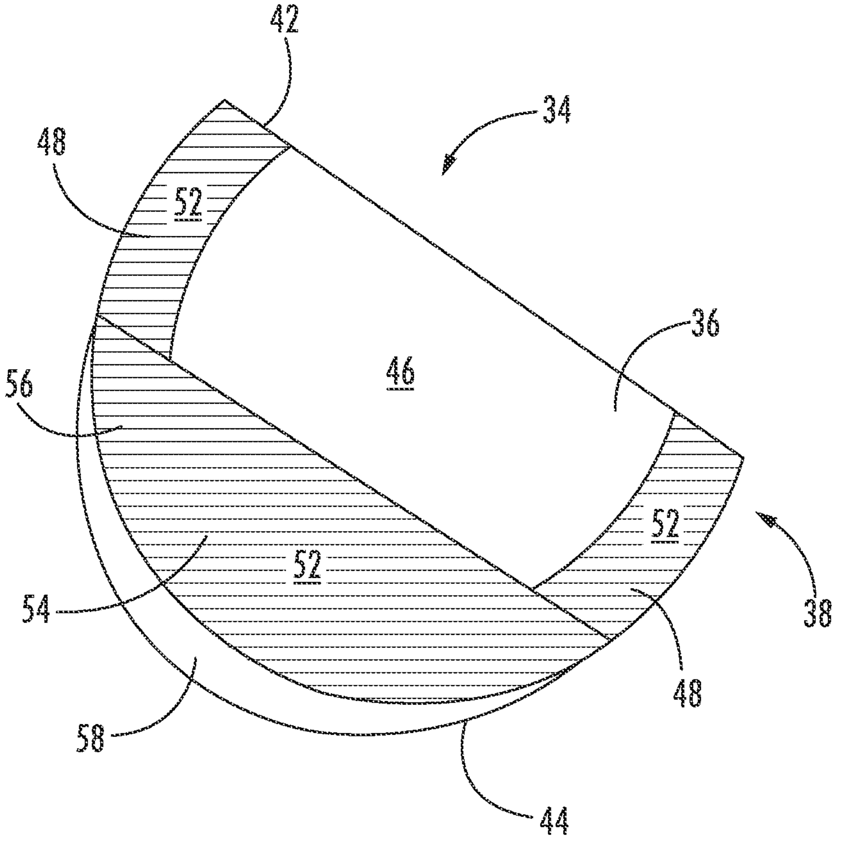
FIG. 2 is a plan view of the back side of the top cover of the nursing pad system.
Figure 3:
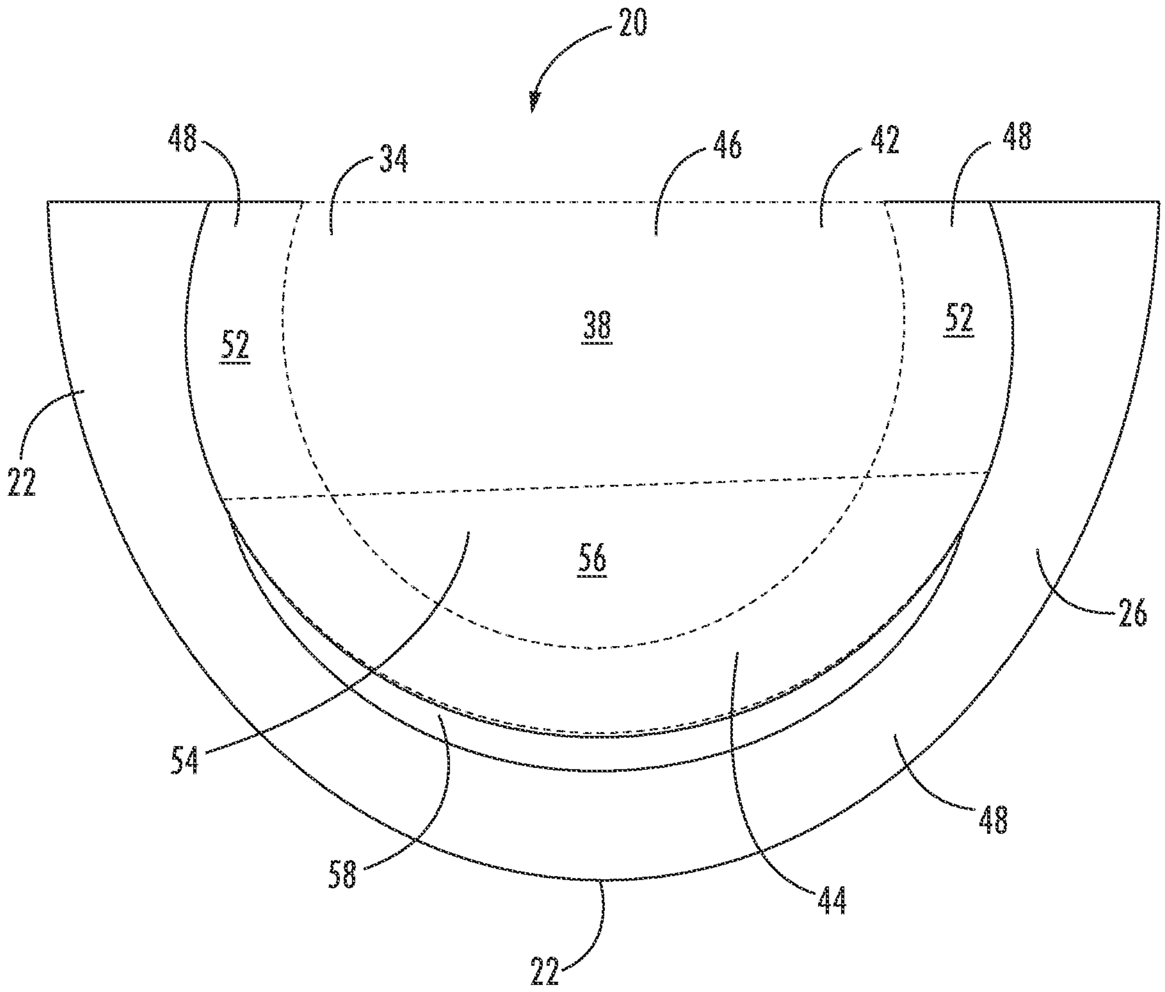
FIG. 3 is a plan view of the front side of the top and base components secured together, with dotted lines showing the unseen peripheral extents.
Figure 10:
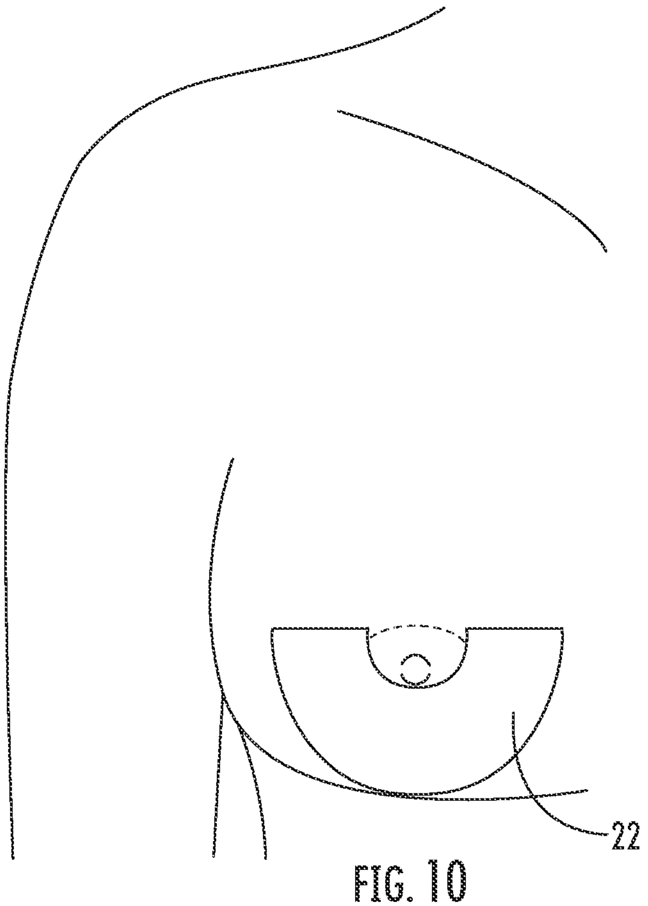
FIG. 10 is a perspective view of the base component adhesively secured about the nipple with the top cover removed.
Figure 11:
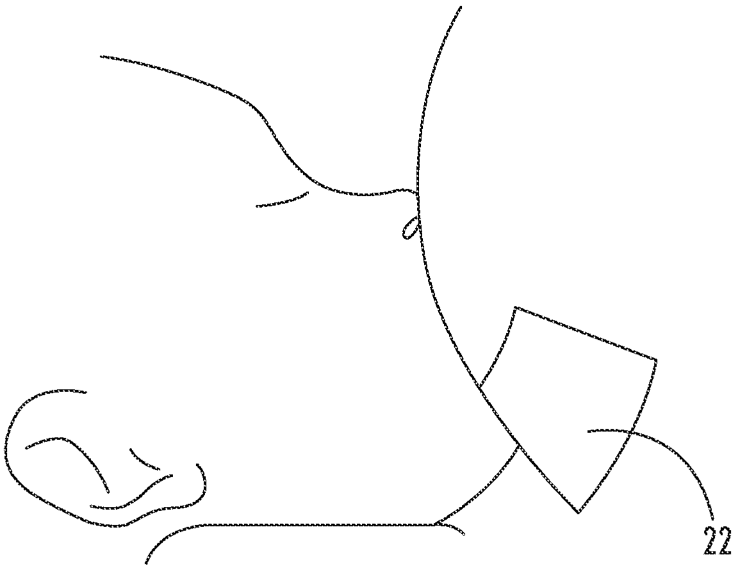
FIG. 11 is a perspective view of the base component adhesively secured about the breast with the top cover removed to allow for breastfeeding.
Figure 12A:
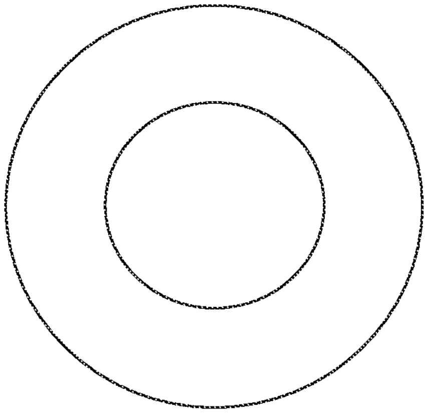
FIGS. 12*a*-12*e* are alternative configurations for the base component.
Figure 12B:
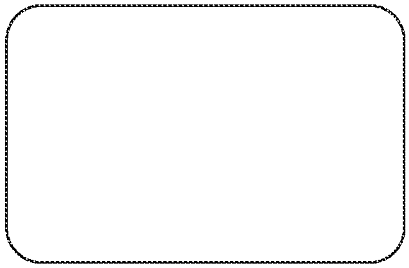
Figure 12C:
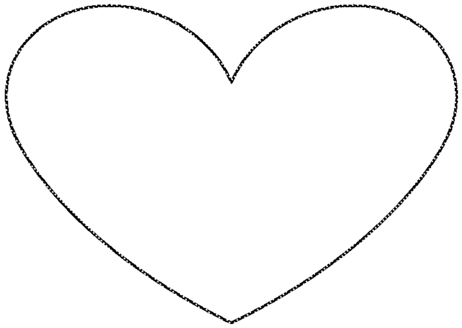
Figure 12D:
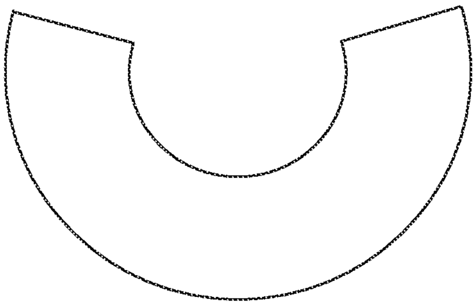
Figure 12E:
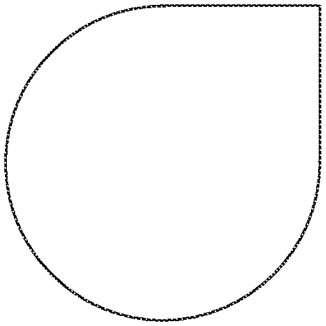

FIGS. 1-2 illustrate the back sides of the lower base component (22) and the removable top cover (34) of the nursing pad system (20). In one non-limiting embodiment, base (22) is U-shaped and includes inner and outer surfaces (24, 26) and an opened, semi-circular interior area (28). The shape of base (22) and the semi-circular interior area (28) allows base (22) to both conform to the mother's breast and surround the nipple. As most clearly illustrated in FIG. 10, when properly positioned, the opened area (28) forms a space for the mother's nipple. In order to secure base (22) to the skin, a low trauma adhesive (32), such as a silicone gel, is applied to the inner surface (24) of base (22). This allows base (22) to be secured to, and removed from, the breast without damaging or irritating the user's skin. Although a silicone gel is preferred, the low trauma adhesive can be any of a variety of silicone, acrylic, hydrogel, hydrocolloid, or acrylic hybrid based adhesives.

With reference to FIG. 2, the back side of top cover (34) is depicted. Top cover (34) is defined by inner/outer surfaces (36, 38) and upper/lower extents (42, 44). Top cover (34) further includes an interior area (46) that is formed from an absorbent material. Suitable absorbent materials include polyester, lyocell, wool, cotton, nylon, hydrocolloid, hydrogel, bamboo, microfiber, lycra, polyurethane, or foam.

Outer surface (38) of top cover (34), by contrast, is formed from a flexible, water proof or leak proof material, such as a polymer. Other suitable water proof materials for outer surface (38) include cotton, polyester, lyocell, polyurethane, polyethelyene, rubber, silicone, PVC, treated fabrics, vinyl, wool, bamboo, foam, and combinations thereof. Ideally, the material is selected to prevent milk from seeping through the cover and onto the wearer's clothing. Top cover (34) further includes opposing peripheral areas (48) that are used in securing top cover (34) to base (22). More specifically, a strong bond adhesive (52), such as an acrylic or natural rubber based adhesive, is applied to these opposing peripheral areas (48). These opposing peripheral areas (48) are then adhesively secured to the outer surface (26) of base (22). The strong bond adhesive can be any of a variety of acrylic, hydrocolloid, or acrylic hybrid based adhesives.

The inner surface (36) of top cover (34) further includes a pocket (54). As illustrated in FIG. 2, pocket (54) is formed at the lower extent (44) of the inner surface (36) of top cover (34). In the depicted embodiment, pocket (54) is formed by securing a semi-circular shaped polymer layer to the inner surface (36). More specifically, the periphery of this semi-circular layer is adhered to the inner surface (36). The bond between the semi-circular layer and inner surface (36) can be formed via a strong bond adhesive. The semi-circular layer likewise includes an interior surface (56) that is coated with the strong bond adhesive (52) and is adhered to the outer surface (26) of the base (22). When so secured, the semi-circular layer forms a pocket (54) upon inner surface (36) of top cover (34) and at a location that is immediately below the absorbent interior area (46). This allows milk to either be absorbed by the interior area (46) or collected within pocket (54).

Figure 5:
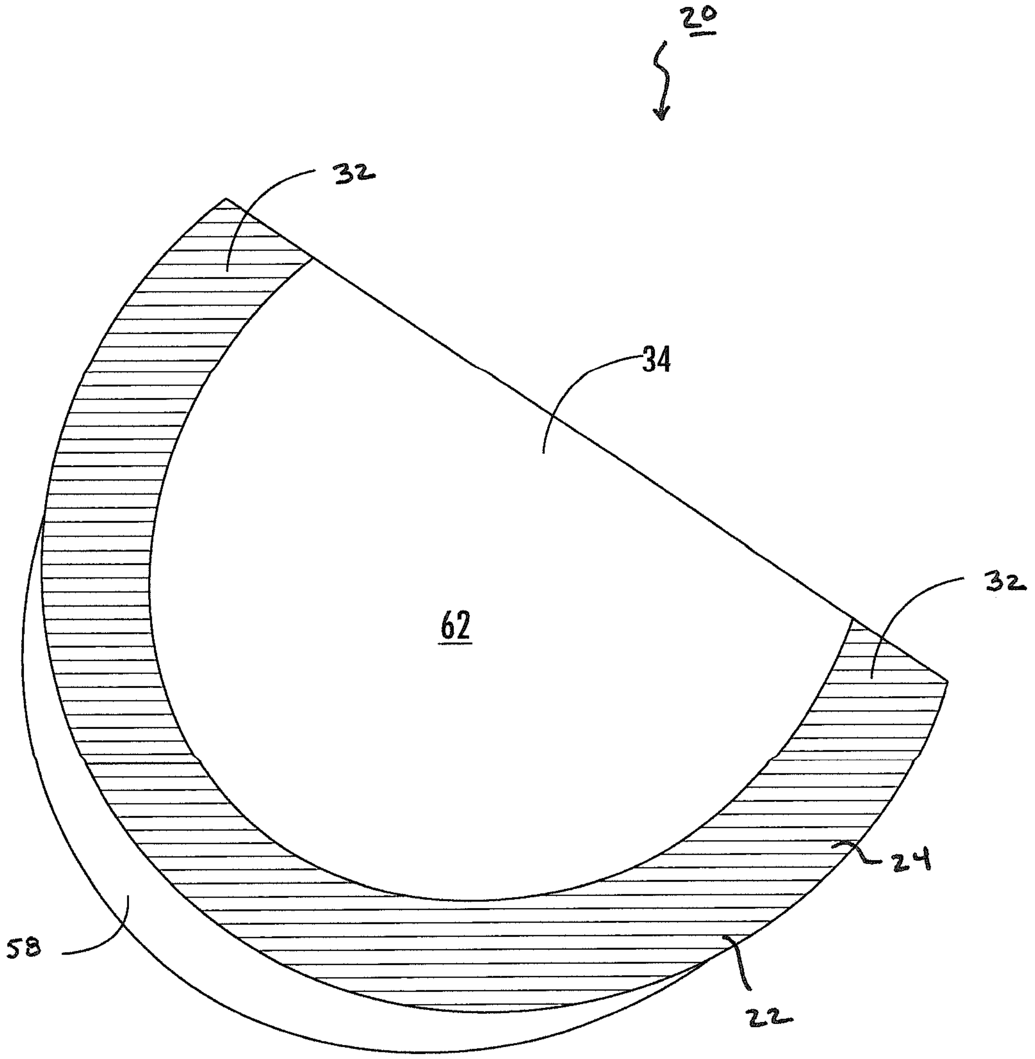
FIG. 5 is a plan view of an alternative embodiment of the top cover and base components.
Figure 6:
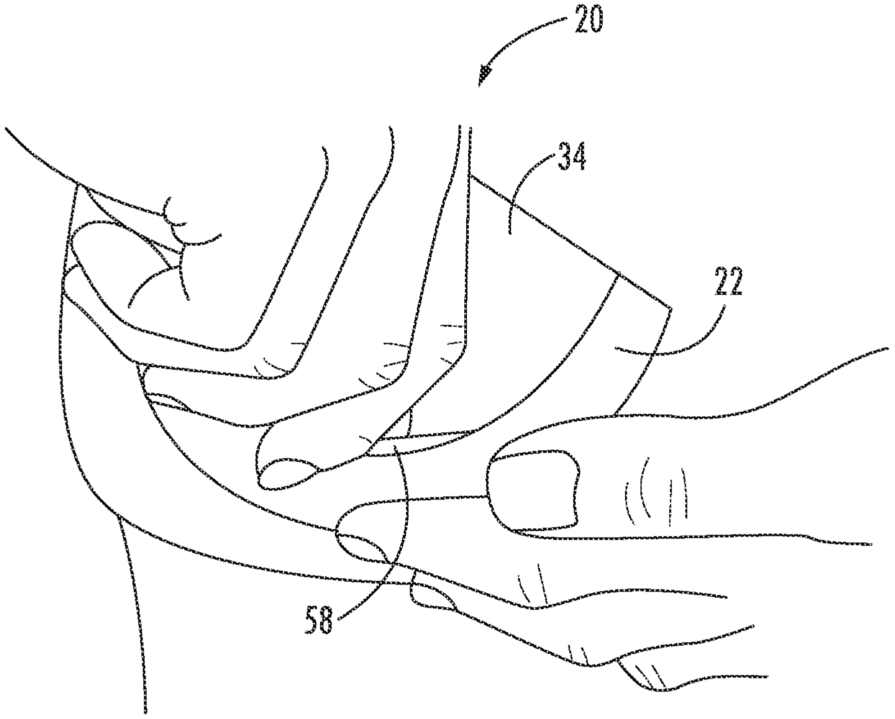
FIG. 6 is a perspective view of the top cover being removed from the base component.
Figure 7:
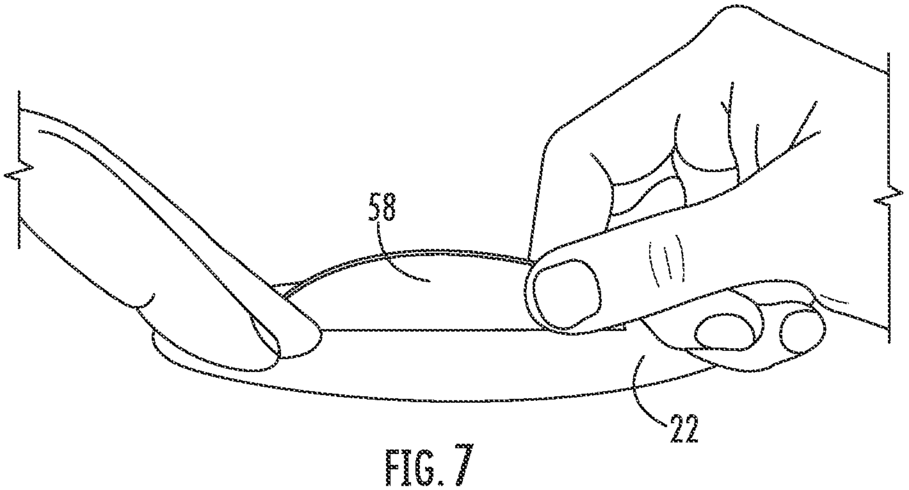
FIG. 7 is a perspective view of the top cover being removed from the base component.
Figure 8:
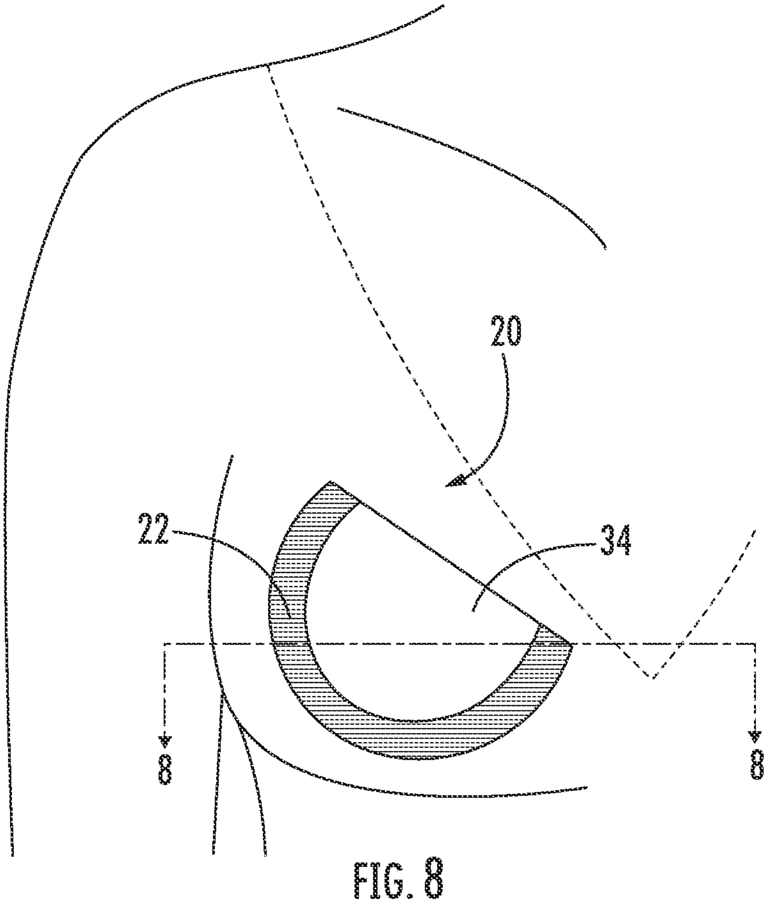
FIG. 8 is a perspective view of the nursing pad system adhesively secured to a breast.
Figure 9:
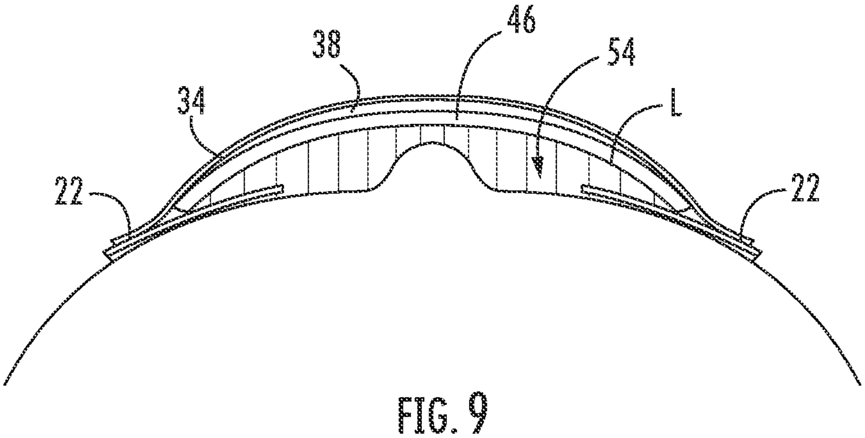
FIG. 9 is a sectional view taken along line 8-8 of FIG. 8.

Pocket (54) can be alternatively formed without the use of an additional layer of material. Namely, as illustrated in FIG. 5, a pocket (62) can be formed by adhesively joining the peripheral edges of top cover (34) to the peripheral edges of lower base (22). This embodiment would form a lager pocket between the lower base (22) and top cover (34). Regardless of how pocket (52) is formed, a release tab (58) is formed at the lower extent (44) of the top cover (34). As illustrated in FIGS. 5-6, this release tab (58) is designed to be grasped by the user so they can easily peel the top cover (34) off the lower base (22).

Figure 4:
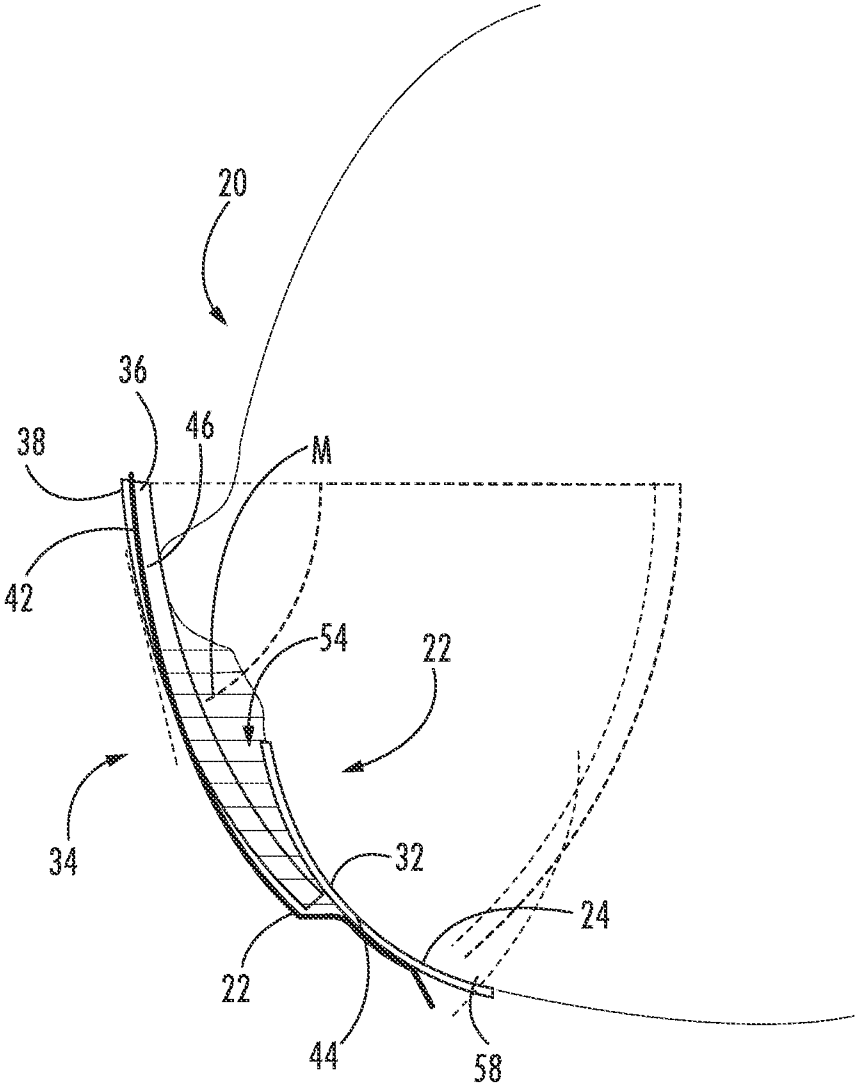
FIG. 4 is a side sectional view of the top cover and base components secured to a breast, with dotted lines showing unseen peripheral extents.

With the nursing pad system (20) in position, the disposable top cover (34) is adhesively secured by joining peripheral areas (48) to the outer surface (26) of base (22). This is preferably achieved via a strong bond adhesive (52). Pocket (54) is adhesively secured to the lower extent outer surface (26) of base (22) in a similar fashion. When so positioned, the mother's nipple is positioned beneath the interior area (46) of the disposable top cover (36). Additionally, as illustrated in FIG. 4, pocket (54) is positioned below the nipple. This allows milk to be absorbed by the material of interior area (46) and also permits milk to accumulate within pocket (54). When top cover (36) becomes saturated, release tab (58) can be used to separate the top cover (34) from base (22). Top cover (36) would likewise be removed to expose the nipple as needed for feedings.

Figure 13:
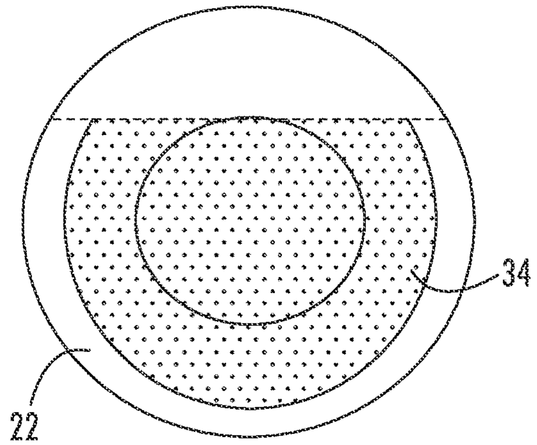
FIG. 13 is a plan view of an embodiment utilizing a circular base pad.
Figure 15:
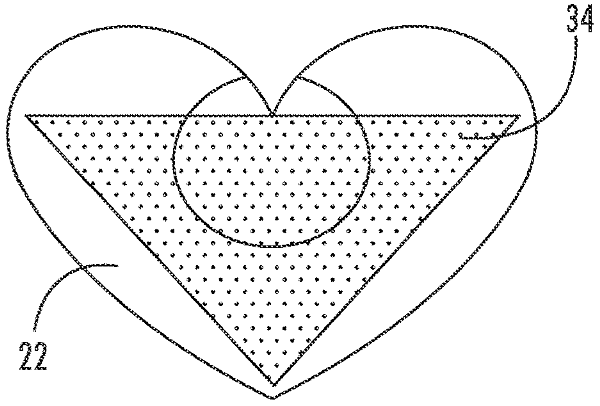
FIG. 15 is a plan view of an embodiment utilizing a heart shaped base pad.
Figure 14:
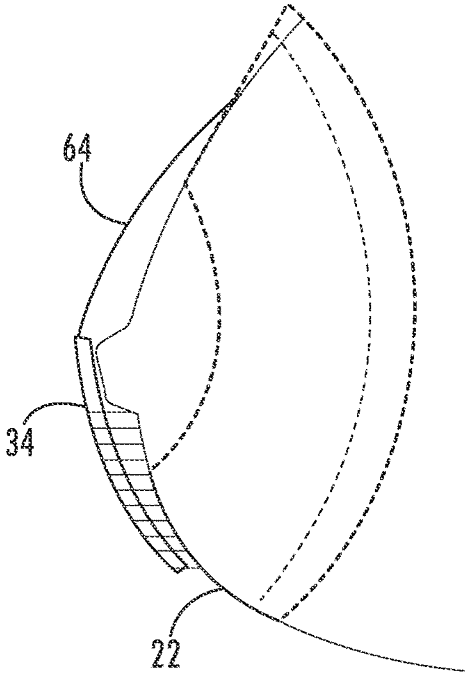
FIG. 14 is a side sectional view of an embodiment utilizing a circular base pad.
Figure 16:
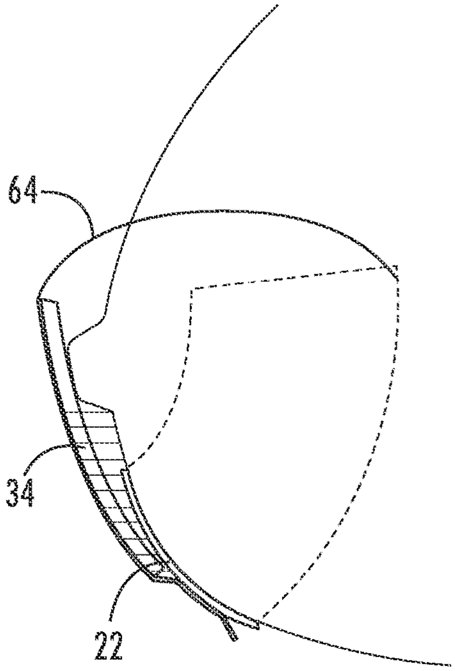
FIG. 16 is a side sectional view of an embodiment utilizing a heart shaped base pad.

Although base (22) is illustrated as being U-shaped, it is within the scope of the present disclosure to use other shapes and configurations. FIGS. 12*a*-12*e* illustrate a few of the alternatives shapes for base (22). Similarly, FIGS. 13 and 15 illustrate some alternative shapes for the top cover (34). As illustrated in FIGS. 14-16, a flap (64) can extend to between the upper extent of the top cover and the breast. Flap (64) operates both as a privacy shield and creates a barrier for the accumulating milk.

The system of the present disclosure can also be presented in the form of a kit. The kit comprises a single container housing one or more bases (22) and a plurality of covers (34). The kit would thereby provide a nursing mother with a large number of disposable covers (34), allowing them to be easily removed and replaced after becoming saturated with milk. For this reason, it is envisioned that the kit would include a greater number of disposable covers (34) and a lesser number of bases (22).

Although this disclosure has been described in terms of certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A nursing pad system adapted for use upon a breast, the nursing pad system comprising:

a base having a base inner surface, a base outer surface, and a first adhesive applied to the base inner surface for removably securing the base to the breast; and a cover including a cover inner surface attached to the base outer surface along a periphery of the cover inner surface with a second adhesive, the cover inner surface, base outer surface, and periphery defining an open interior area therebetween, the open interior area including an absorbent material and a pocket for capturing breast milk;

wherein the cover is disposable by being adhered to the base outer surface with the second adhesive in such a way that the cover is removable from the base outer surface.

2. The nursing pad system of claim 1, wherein the first adhesive is a low trauma adhesive.

3. The nursing pad system of claim 1, wherein the second adhesive is a strong bond adhesive.

4. The nursing pad system of claim 1, wherein the base is configured to fit about a nipple.

5. The nursing pad system of claim 1, wherein the pocket is positioned beneath a nipple of a breast feeding mother.

6. The nursing pad system of claim 1, wherein the pocket is positioned below the absorbent material.

7. The nursing pad system of claim 1, wherein the pocket is formed by securing a layer of material to the cover inner surface.

8. The nursing pad system of claim 1, wherein:

the base includes a nipple-receiving area configured to at least partially surround a nipple and leave the nipple exposed when adhered to the breast; and the cover inner surface covers the nipple-receiving area.

9. The nursing pad system of claim 1, wherein the second adhesive is configured to permit the cover to be removed from the base while the base is adhered to the breast.

10. The nursing pad system of claim 1, wherein an upper extent of the cover is open to the interior area.

11. The nursing pad system of claim 1, wherein the periphery of the cover inner surface is attached to a bottom perimeter of the base outer surface.

12. A nursing pad system adapted for use upon a breast, the nursing pad system comprising:

a base having a base inner surface, a base outer surface, and a first adhesive applied to the base inner surface for removably securing the base to the breast; and a cover including a cover inner surface attached to the base outer surface along a periphery of the cover inner surface with a second adhesive, the cover inner surface, base outer surface, and periphery defining an open interior area therebetween, the open interior area including an absorbent material and a pocket for capturing breast milk;

wherein the base includes a nipple-receiving area configured to at least partially surround a nipple and leave the nipple exposed when adhered to the breast; and the cover inner surface covers the nipple-receiving area.

13. The nursing pad system of claim 12, wherein the first adhesive is a low trauma adhesive.

14. The nursing pad system of claim 12, wherein the second adhesive is a strong bond adhesive.

15. The nursing pad system of claim 12, wherein the cover is disposable by being adhered to the base outer surface with the second adhesive in such a way that the cover is removable from the base outer surface.

16. The nursing pad system of claim 12, wherein the pocket is positioned beneath a nipple of a breast feeding mother.

17. The nursing pad system of claim 12, wherein the pocket is positioned below the absorbent material.

18. The nursing pad system of claim 12, wherein the pocket is formed by securing a layer of material to the cover inner surface.

19. The nursing pad system of claim 12, wherein the second adhesive is configured to permit the cover to be removed from the base while the base is adhered to the breast.

20. The nursing pad system of claim 12, wherein an upper extent of the cover is open to the interior area.

21. The nursing pad system of claim 12, wherein the periphery of the cover inner surface is attached to a bottom perimeter of the base outer surface.

22. A nursing pad system adapted for use upon a breast, the nursing pad system comprising:

a base having a base inner surface, a base outer surface, and a first adhesive applied to the base inner surface for removably securing the base to the breast; and a cover including a cover inner surface attached to the base outer surface along a periphery of the cover inner surface with a second adhesive, the cover inner surface, base outer surface, and periphery defining an open interior area therebetween, the open interior area including an absorbent material and a pocket for capturing breast milk;

wherein the second adhesive is configured to permit the cover to be removed from the base while the base is adhered to the breast.

23. The nursing pad system of claim 22, wherein the first adhesive is a low trauma adhesive.

24. The nursing pad system of claim 22, wherein the second adhesive is a strong bond adhesive.

25. The nursing pad system of claim 22, wherein the base is configured to fit about a nipple.

26. The nursing pad system of claim 22, wherein the pocket is positioned beneath a nipple of a breast feeding mother.

27. The nursing pad system of claim 22, wherein the pocket is positioned below the absorbent material.

28. The nursing pad system of claim 22, wherein the pocket is formed by securing a layer of material to the cover inner surface.

29. The nursing pad system of claim 22, wherein:

the base includes a nipple-receiving area configured to at least partially surround a nipple and leave the nipple exposed when adhered to the breast; and the cover inner surface covers the nipple-receiving area.

30. The nursing pad system of claim 22, wherein an upper extent of the cover is open to the interior area.

31. The nursing pad system of claim 22, wherein the periphery of the cover inner surface is attached to a bottom perimeter of the base outer surface.

32. A nursing pad system adapted for use upon a breast, the nursing pad system comprising:

a base having a base inner surface, a base outer surface, and a first adhesive applied to the base inner surface for removably securing the base to the breast; and a cover including a cover inner surface attached to the base outer surface along a periphery of the cover inner surface with a second adhesive, the cover inner surface, base outer surface, and periphery defining an open interior area therebetween, the open interior area including an absorbent material and a pocket for capturing breast milk;

wherein an upper extent of the cover is open to the interior area.

33. The nursing pad system of claim 32, wherein the first adhesive is a low trauma adhesive.

34. The nursing pad system of claim 32, wherein the second adhesive is a strong bond adhesive.

35. The nursing pad system of claim 32, wherein the cover is disposable by being adhered to the base outer surface with the second adhesive in such a way that the cover is removable from the base outer surface.

36. The nursing pad system of claim 32, wherein the base is configured to fit about a nipple.

37. The nursing pad system of claim 32, wherein the pocket is positioned beneath a nipple of a breast feeding mother.

38. The nursing pad system of claim 32, wherein the pocket is positioned below the absorbent material.

39. The nursing pad system of claim 32, wherein the pocket is formed by securing a layer of material to the cover inner surface.

40. The nursing pad system of claim 32, wherein:

the base includes a nipple-receiving area configured to at least partially surround a nipple and leave the nipple exposed when adhered to the breast; and the cover inner surface covers the nipple-receiving area.

41. The nursing pad system of claim 32, wherein the second adhesive is configured to permit the cover to be removed from the base while the base is adhered to the breast.

42. The nursing pad system of claim 32, wherein the periphery of the cover inner surface is attached to a bottom perimeter of the base outer surface.

* * * * *